United States Patent [19]

Wurtman et al.

[11] Patent Number: 4,885,312

[45] Date of Patent: Dec. 5, 1989

[54] METHOD FOR ENHANCING THE EFFECT OF INDIRECT-ACTING SYMPATHOMIMETIC AMINES

[75] Inventors: Richard J. Wurtman, Boston; Timothy J. Maher, Milton, both of Mass.

[73] Assignee: Massachusetts Institute of Technology, Cambridge, Mass.

[21] Appl. No.: 947,208

[22] Filed: Dec. 29, 1986

Related U.S. Application Data

[62] Division of Ser. No. 845,141, Mar. 27, 1986, Pat. No. 4,673,689, which is a division of Ser. No. 780,054, Sep. 25, 1985, Pat. No. 4,598,094.

[51] Int. Cl.$^4$ ............................................ A61K 31/195
[52] U.S. Cl. .................................................... 514/561
[58] Field of Search ................................. 514/561, 567

[56] References Cited

U.S. PATENT DOCUMENTS 4,327,112  4/1982  Wurtman ............................ 514/567

OTHER PUBLICATIONS

Merck Index 9th Ed., 1976–p. 471.

Primary Examiner—Stanley J. Friedman
Attorney, Agent, or Firm—Paul J. Cook

[57] ABSTRACT

Tyrosine or a tyrosine precursor is administered concomitantly with an indirect-acting sympathomimetic amine drug to increase the level of norepinephrine that can be released in sympathetic neuron synapses.

5 Claims, No Drawings

METHOD FOR ENHANCING THE EFFECT OF INDIRECT-ACTING SYMPATHOMIMETIC AMINES

This is a divisional of co-pending application Ser. No. 845,141 filed on Mar. 27, 1986, now U.S. Pat. No. 4,673,689, which is a divisional of Ser. No. 780,054 filed on Sept. 25, 1985, now U.S. Pat. No. 4,598,084.

BACKGROUND OF THE INVENTION

This invention relates to a method and composition for enhancing the desirable effects of drugs comprising indirect-acting sympathomimetic amines.

Indirect-acting sympathomimetic amines function by releasing stored norepinephrine from sympathetic nerve endings. The major problem with their use is that after a few doses, they often stop functioning, i.e., tachyphylaxis sets in. Tachyphyl-axis is known to be associated with partial depletion of the norepinephrine in the nerve endings, leading to the supposition that there are releasable and non-releasable pools of norepinephrine and that when the drugs cease functioning, it is because the releasable pools have been severely depleted.

Prior to the present invention, tyrosine or a tyrosine precursor has been administered concomitantly with a drug in order to enhance the effectiveness of the drug or to reduce or eliminate undesirable effects associated with the drug.

U.S. Pat. No. 4,224,343 discloses the administration of tyrosine or a tyrosine precursor concomitant with a drug which has the undesirable effect of increasing prolactin secretion, thereby to decrease prolactin secretion. Examples of such drugs are reserpine, aldomet and clonidine.

U.S. Pat. No. 4,271,192 discloses that tyrosine can be administered with drugs known to reduce the risk of ventricular fibrilation in order to potentiate the drugs' activity. Representative suitable drugs include procainamide, quinidine, propranolol and diphenylhydantoin.

U.S. Pat. No. 4,327,112 discloses the administration of tyrosine or a tyrosine precursor to a human together with a drug known to increase blood pressure in order to potentiate the dugus activity for increasing blood pressure. Typical drugs disclosed are neosynephrine, calcium chloride, ephedrine, dopamine and dorepinephrine.

U.S. Pat. No. 4,470,987 also disclosed the use of the combination of tyrosine and a drug in order to prevent ventricular fibrilation.

It would be desirable to provide a means for preventing tachyphylaxis with indirect-acting sympathomimetic amine drugs so that the drugs could be rendered useful for long periods.

SUMMARY OF THE INVENTION

The present invention provides a method and composition for preventing tachyphylaxis of indirect-acting sympathomimetic amine drugs. Tyrosine or a tyrosine precursor is administered concomitantly with the drug and the tyrosine is converted to norepinephrine in a foam which renders it releasable in sympathetic nerve synapses. The result of utilizing tyrosine prevents tachyphylaxis of the drug.

DETAILED DESCRIPTION OF SPECIFIC EMBODIMENTS

In accordance with this invention, tyrosine or a tyrosine precursor such as phenylalanine is administered concomitnatly with an indirect-acting sympathomimetic amine drug, thereby to increase the level of norepinephrine which can be released in sympathetic neuron synapses.

Representative indirect-acting sympathomimetic amine drugs which can be utilized in the present invention include ephedrine, metaraminol, hydroxyamphetamine or mephentermine which are normally administered intravenously; pseudoephedrine, phenylpropanolamine, amphetamine, or methoxyphenamine which are administered orally or by inhalation or oxymetazoline, propylehexedrine,

We claim:

1. The process for preventing tachyphylaxis of an indirect acting sympathomimetic amine drug selected from the group consisting of metaraminol, pseudoephedrine and methoxyphenamine which comprises administering to a patient concomitantly with said drug, a catecholamine precursor selected from the group consisting of tyrosine, a tyrosine precursor or a mixture of tyrosine and a tyrosine precursor to obtain a tyrosine blood plasma concentration between about 15 and about 100 µg/ml.

2. The process of claim 1 wherein said catecholamine precursor is tyrosine.

3. The process of either claim 1 or 2 wherein said drug is metaraminol.

4. The process of either claim 1 or 2 wherein said drug is pseudoephedrine.

5. The process of either claim 1 or 2 wherein said drug is methoxyphenamine.

* * * * *